United States Patent [19]

McCloskey et al.

[11] Patent Number: 5,672,776
[45] Date of Patent: Sep. 30, 1997

[54] METHOD FOR PURIFYING 1,1,1-TRIS(4-HYDROXYPHENYL)-ALKANES

[75] Inventors: Patrick Joseph McCloskey, Watervliet; Julia Lam Lee, Niskayuna, both of N.Y.

[73] Assignee: General Electric Company, Schenectady, N.Y.

[21] Appl. No.: 722,282

[22] Filed: Sep. 27, 1996

[51] Int. Cl.$^6$ .............................. C07C 37/68; C07C 39/12
[52] U.S. Cl. .............................. 568/756; 568/720
[58] Field of Search .............................. 568/720, 724, 568/756

[56] References Cited

U.S. PATENT DOCUMENTS 4,992,598  2/1991  Strutz .
5,130,467  7/1992  Mott .
5,202,505  4/1993  Murphy .

*Primary Examiner*—José G. Dees
*Assistant Examiner*—Karl J. Puttlitz, Jr.
*Attorney, Agent, or Firm*—William H. Pittman

[57] ABSTRACT

Tris(4-hydroxyphenyl)alkanes such as 1,1,1-tris(4-hydroxyphenyl)ethane are purified by formation of an adduct with a molar excess of a $C_{1-4}$ primary alkyl tertiary amine, preferably triethylamine. Adduct formation is preferably effected in a polar organic solvent such as methanol. The pure tris(4-hydroxyphenyl)alkane may be recovered from the adduct by thermal or aqueous acid-promoted cracking.

15 Claims, No Drawings

5,672,776

METHOD FOR PURIFYING 1,1,1-TRIS(4-HYDROXYPHENYL)-ALKANES

BACKGROUND OF THE INVENTION

This invention relates to the purification of 1,1,1-tris(4-hydroxyphenyl)alkanes and especially 1,1,1-tris(4-hydroxyphenyl)ethane.

The subject compounds, especially the ethane compound which is hereinafter sometimes designated "THPE", are useful as branching agents for polycarbonates. For this purpose, they may be incorporated in reaction mixtures also containing dihydroxyaromatic compounds such as bisphenol A and carbonate sources such as phosgene or diphenyl carbonate. The compounds are commonly prepared by the reaction of 4-hydroxyacetophenone and its homologs with phenol, said reaction being analogous to the reaction of phenol with acetone to form 2,2-bis(4-hydroxyphenyl) propane, also known as "bisphenol A". As disclosed in copending provisional application Ser. No. 60/32,802 and complete application Ser. No. 08/718,287, the disclosures of which are incorporated by reference herein, a second method for preparing THPE (recovered in admixture with bisphenol A) is by the reaction under acidic conditions of phenol with 2,4-pentanedione.

According to U.S. Pat. No. 4,992,598, THPE produced by the reaction of 4-hydroxyacetophenone with phenol can be purified by a series of washes with methanol-water variously containing at least one of THPE and sodium borohydride. In general, numerous washing steps of this type apparently need to be employed. An alternative purification method which does not require so many steps is desirable.

SUMMARY OF THE INVENTION

The present invention provides such an alternative purification method. It may be employed to afford a product having an APHA color number of less than 200 from a crude product containing at least about 90% THPE by weight.

The invention is a method for further purifying a tris(4-hydroxyphenyl)alkane of at least about 90% by weight purity which comprises:

forming an adduct by contacting said tris(4-hydroxyphenyl)alkane with a molar excess of a $C_{1-4}$ primary alkyl tertiary amine, and recovering purified tris(4-hydroxyphenyl)alkane from said adduct by thermal or aqueous acid-promoted cracking.

DETAILED DESCRIPTION, PREFERRED EMBODIMENTS

The tris(4-hydroxyphenyl)alkanes which may be purified by the method of this invention include, as a genus, those compounds capable of preparation by the reaction of phenol with 4-hydroxyacetophenone and its higher homologs, such as the corresponding propiophenone and butyrophenone. The preferred compound is THPE.

According to the invention, THPE having a purity of at least about 90% by weight is first obtained. In the case of the 4-hydroxyacetophenone preparation method, THPE of the required purity may be obtained by removing by-product phenol by filtration after adjusting the water content, as disclosed in the aforementioned U.S. Pat. No 4,992,598. In the case of the 2,4-pentanedione synthesis method, slurrying in a chlorinated alkane such as methylene chloride followed by filtration can afford a solid product of the requisite purity.

The essential purification step is the formation of an adduct between THPE and a $C_{1-4}$ primary alkyl tertiary amine such as trimethylamine, triethylamine or tri-n-butylamine. Triethylamine is preferred and will often be referred to hereinafter; however, it should be understood that other tertiary amines as describe may be substituted therefor.

The adduct is formed by blending the THPE with a molar excess of the amine. A typical molar ratio of amine to THPE is at least about 1.5:1, preferably at least about 2:1 and most preferably about 2.4–2.8:1. The adduct thus formed comprises equimolar proportions of the amine and THPE.

The precise nature of the adduct is not known. It may be a salt or complex. In any event, it is readily and conveniently cracked as described hereinafter, to produce THPE of high purity.

It is possible to merely blend the two reagents, THPE and amine, in proportions such that the amine serves as a solvent. However, the adduct then sometimes "crashes" from the mixture in clumps which are difficult to process further. Therefore, it is usually preferred to employ a separate solvent, most often a polar organic liquid such as a $C_{1-4}$ alkanol; methanol is preferred and is generally referred to hereinafter. The alkanol may contain a decolorizing proportion, typically about 0.01–0.10% by weight, of an alkali metal borohydride or dithionite ($MBH_4$ or $M_2S_2O_3$, respectively, where M is an alkali metal), as a decolorizing agent; sodium borohydride is preferred.

After dissolution of the crude THPE in the alkanol, the triethylamine may be introduced at a temperature in the range of about 20°–40° C. If a relatively large excess of triethylamine (e.g., a molar ratio of triethylamine to THPE of at least about 2:1), the adduct crystallizes slowly. Further crops of adduct may be obtained by allowing the mixture to stand at ambient temperature and/or by adding water, typically in a 1:1 molar ratio to methanol. Smaller proportions of triethylamine will cause adduct to form but it may remain in solution until precipitated by addition of water. When formation and crystallization of a crop of adduct is complete, the adduct may be removed by filtration.

Following its isolation, the adduct may be cracked by heating in vacuum to a temperature of at least 80° C. and preferably about 85°–100° C., whereupon the triethylamine is easily removed by volatilization. Alternatively, cracking may be achieved by contact with aqueous acid at a temperature in the range of about 20°–50° C., preferably about 20°–30° C. Typical acids which may be employed are the common mineral acids and acetic acid, at concentrations of about 1–2M. The free THPE precipitates from the acidic solution and may be recovered by conventional means. Its purity is generally at least about 99% by weight, and its APHA color number is usually no higher than about 200.

The method of the invention is illustrated by the following examples.

EXAMPLE 1

A 500-ml round-bottomed flask equipped with a stirrer was charged with 94 g (1 mole) of phenol, 1.50 g (14 mmol) of 3-mercaptopropionic acid and 100 mg of p-terphenyl as an internal standard. The reaction mixture was warmed to 60° C., whereupon the phenol melted. Hydrogen chloride gas was bubbled through the mixture for 30 minutes, after which it was cooled to room temperature and 8.33 g (83 mmol) of 2,4-pentanedione was added dropwise over 30 minutes. The mixture was heated to 40° C. with occasional addition of hydrogen chloride gas, during which time it became very viscous and a precipitate slowly formed. Stirring was continued overnight at room temperature.

A portion of the mixture was filtered, yielding an orange solid shown by analysis to be a mixture of THPE and bisphenol A. To the remainder of the mixture was added 300 ml of methylene chloride, whereupon a pink solid precipitated and was collected by filtration. Liquid chromatographic analysis showed the solid to comprise about 92% by weight THPE, 6.1% bisphenol A and 1% phenol.

A 63.5-g sample of the crude THPE (191 mmol of THPE) was dissolved in 250 ml of methanol to form a light amber solution. Triethylamine, 62.5 ml (449 mmol) was added, whereupon the color of the solution changed to faint pink. A white solid crystallized slowly as the mixture was stirred over 45 minutes. The solid was removed by filtration and was found upon analysis to be the desired adduct of THPE and triethylamine. Upon standing for an additional 2 hours, the filtrate deposited a second crop which was similarly removed by filtration.

The adduct was slurried in a 1.5M aqueous acetic acid solution for 1 hour. Upon filtration, THPE was isolated as a snow white solid.

EXAMPLE 2

The procedure of Example 1 was repeated and water, 250 ml, was added slowly to the mother liquor from the second crop of crystals, resulting in further precipitation of white solid which was collected by filtration. The various crops were washed with water, dried and combined.

EXAMPLE 3

The procedure of Example 1 was repeated, except that the methanol contained 0.05% by weight sodium borohydride.

EXAMPLE 4

The procedure of Example 3 was repeated, using crude THPE prepared by the reaction of phenol with 4-hydroxyacetophenone.

EXAMPLE 5

The procedure of Example 1 was repeated except that the methanol was omitted and the crude THPE was treated with neat triethylamine. Clumps of adduct "crashed" from the mixture.

The results of Examples 1–5 are listed in the following table.

| Example | THPE recovery, % | THPE purity, % | APHA color no. |
|---|---|---|---|
| 1 | 80 | 99.4 | 179 |
| 2 | 95 | 99.3 | 176 |
| 3 | 86 | 99.4 | 63 |
| 4 | 94 | 99.5 | Light tan |
| 5 | 94 | 99.4 | Pink |

It is apparent that the method of the invention produces very pure THPE in high yield. Color is substantially improved by using sodium borohydride.

What is claimed is:

1. A method for further purifying a tris(4-hydroxyphenyl) alkane of at least about 90% by weight purity which comprises:

forming an adduct by contacting said tris(4-hydroxyphenyl)alkane with a molar excess of a $C_{1-4}$ primary alkyl tertiary amine, and recovering purified tris(4-hydroxyphenyl)alkane from said adduct by thermal or aqueous acid-promoted cracking.

2. A method according to claim 1 wherein the tris(4-hydroxyphenyl)alkane is 1,1,1-tris(4-hydroxyphenyl)ethane.

3. A method according to claim 2 wherein the tertiary amine is triethylamine.

4. A method according to claim 3 wherein adduct formation is conducted in a polar organic liquid as solvent.

5. A method according to claim 4 wherein the polar organic liquid is a $C_{1-4}$ alkanol.

6. A method according to claim 5 wherein the alkanol is methanol.

7. A method according to claim 6 wherein the methanol contains a decolorizing proportion of an alkali metal borohydride or dithionite.

8. A method according to claim 7 wherein the alkali metal borohydride or dithionite is sodium borohydride.

9. A method according to claim 6 wherein the molar ratio of triethylamine to 1,1,1-tris(4-hydroxyphenyl)ethane is at least about 1.5:1.

10. A method according to claim 6 wherein the molar ratio of triethylamine to 1,1,1-tris(4-hydroxyphenyl)ethane is in the range of about 2.4–2.8:1.

11. A method according to claim 6 wherein multiple crops of adduct are caused to precipitate.

12. A method according to claim 11 wherein precipitation is caused by allowing the reaction mixture containing said adduct to stand.

13. A method according to claim 11 wherein precipitation is caused by adding water to the reaction mixture containing said adduct.

14. A method according to claim 3 wherein cracking of said adduct is effected by heating in vacuum to a temperature of at least 80° C., whereupon the triethylamine is removed by volatilization.

15. A method according to claim 3 wherein cracking of said adduct is effected by contact with aqueous acid at a temperature in the range of about 20°–50° C.

* * * * *